(12) United States Patent
Novelli

(10) Patent No.: US 7,022,140 B2
(45) Date of Patent: Apr. 4, 2006

(54) ACROMIOCLAVICULAR JOINT PROSTHESIS

(76) Inventor: Angelo Novelli, 30 Lombardy Rd., Turnersville, NJ (US) 08012

( * ) Notice: Subject to any disclaimer, the term of this patent is extended or adjusted under 35 U.S.C. 154(b) by 54 days.

(21) Appl. No.: 10/752,559

(22) Filed: Jan. 8, 2004

(65) Prior Publication Data

US 2005/0154469 A1    Jul. 14, 2005

(51) Int. Cl.
*A61F 2/40* (2006.01)
(52) U.S. Cl. ............... 623/19.11; 623/23.41; 606/72
(58) Field of Classification Search ........... 623/18.11, 623/19.11, 19.12, 21.12, 21.13, 21.16, 21.18, 623/23.39, 23.4, 23.41; 606/72–74
See application file for complete search history.

(56) References Cited

U.S. PATENT DOCUMENTS

| | | | | |
|---|---|---|---|---|
| 3,837,008 | A | * | 9/1974 | Bahler et al. ............ 623/21.13 |
| 3,869,730 | A | | 3/1975 | Skobel |
| 3,979,778 | A | | 9/1976 | Stroot |
| 4,550,450 | A | | 11/1985 | Kinnett |
| D285,969 | S | | 9/1986 | Kinnett |
| 4,754,749 | A | * | 7/1988 | Tsou ....................... 606/73 |
| 5,409,490 | A | * | 4/1995 | Ethridge ................... 606/80 |
| 5,944,757 | A | | 8/1999 | Grammont |
| 6,132,467 | A | * | 10/2000 | Keller ..................... 623/18.11 |
| 6,193,758 | B1 | | 2/2001 | Huebner |
| 6,620,197 | B1 | | 9/2003 | Maroney et al. |
| 2002/0099381 | A1 | | 7/2002 | Maroney |
| 2002/0099445 | A1 | | 7/2002 | Maroney et al. |
| 2003/0144738 | A1 | | 7/2003 | Rogalski |

FOREIGN PATENT DOCUMENTS

| | | |
|---|---|---|
| FR | 2541890 | 9/1984 |
| SU | 1489745 A1 * | 6/1989 |
| WO | 93/9733 | 5/1993 |

* cited by examiner

*Primary Examiner*—Bruce E. Snow
(74) *Attorney, Agent, or Firm*—Richard C. Litman

(57) ABSTRACT

The acromioclavicular joint prosthesis of the present invention provides a mechanism for securing the distal or outer end of the clavicle to the acromion of the scapula. The present prosthetic device includes an acromion attachment component, an opposite clavicle attachment component, and an articulated joint between the two components. The intermediate joint may include a "breakaway" component, allowing the joint to be temporarily misaligned in the event that a severe force is applied to the shoulder, rather than damaging the joint or shoulder structure. The breakaway joint may be quickly and easily realigned by a medical professional. The joint may also include a spring loaded shock absorption component as well, to avoid damage to the joint due to excessive tensile forces. Tools and a method for surgically installing and locking the present prosthesis securely to the respective bones of the skeletal structure, are also disclosed.

19 Claims, 11 Drawing Sheets

ACROMIOCLAVICULAR JOINT PROSTHESIS

BACKGROUND OF THE INVENTION

1. Field of the Invention

The present invention relates generally to the medical and surgical fields, and more specifically to an internal prosthesis (endoprosthesis) for the shoulder joint between the acromion extension of the scapula and the outward end of the clavicle. The acromioclavicular joint prosthesis of the present invention serves to reconnect the two bones of this joint, while providing the freedom of movement and shock absorption required.

2. Description of the Related Art

Shoulder injuries occur relatively frequently, and may comprise injury to any of a number of different joints and tissues. While a relatively simple dislocation of the ball of the upper arm bone (humerus) from its glenoid seat in the scapula is perhaps the most common shoulder injury, there are a large number of other injuries which can occur, from breakage of bones in the shoulder area to the tearing of ligaments and other tissues, damage to the joints due to arthritis or other osteal deterioration, etc. In many cases, the shoulder joint is damaged to the extent that it is no longer capable of functioning to anywhere near a normal extent.

As a result, a number of artificial shoulder joints have been developed in the past, as evidenced by the number of earlier patents for such devices. However, none of those devices provide for the repair of a separation between the distal (outward) end of the clavicle and the acromion, which extends outwardly from the scapula. This joint serves to hold the shoulder up in its normal position, among other purposes. When this joint separates, the scapula and its attached humerus tend to drop downwardly and outwardly, as there is no other bone joint connecting the scapula to the remainder of the skeletal structure. At least some form of external support is required for even limited function of the affected joint and limb, with surgical repair being desired.

However, surgical repair does not always prove effective. In many instances, the repaired joint separates again, reverting to the same problem as before the surgery was done. Yet, to the knowledge of the present inventor, no one has developed any form of artificial or prosthetic joint that may be substituted for the damaged acromioclavicular joint for forming a durable repair.

Accordingly, the present invention provides a solution to this problem in the form of an acromioclavicular joint prosthesis which may be used to provide a secure and durable repair to a damaged acromioclavicular shoulder joint. The present prosthesis essentially comprises an acromion attachment component and a clavicle attachment component, with appropriate connection elements therebetween to provide the required freedom of movement for the joint. Means for securing the two attachment components to their respective bones, is also provided.

A discussion of the related art of which the present inventor is aware, and its differences and distinctions from the present invention, is provided below.

U.S. Pat. No. 3,869,730 issued on Mar 11, 1975 to Barry A. Skobel, titled "Surgically Implantable Joint Prosthesis," describes an artificial joint for replacing the shoulder attachment ball of the humerus and its scapular glenoid socket. The prosthetic joint includes a gimbal to provide the necessary degrees of freedom for the joint, as well as perforations to provide for bone ingrowth for more secure attachment as the repair heals. However, the Skobel prosthetic device does nothing to provide for the reattachment of a separated acromioclavicular joint and does not provide a prosthetic joint structure for this joint, as provided by the present invention.

U.S. Pat. No. 3,979,778 issued on Sep. 14, 1976 to Jerome H. Stroot, titled "Shoulder Prosthesis," describes another artificial replacement for the humerus and scapula glenoid joint. Again, no disclosure is made of any form of prosthetic joint for the acromion and clavicle, as addressed by the present invention.

U.S. Pat. No. 4,550,450 issued on Nov. 5, 1985 to James G. Kinnett, titled "Total Shoulder Prosthesis System," describes both a humerus—scapula joint prosthesis and a prosthesis secured to the acromion, with the artificial ball of the humerus bearing against the acromion prosthetic component. However, the acromion component is a relatively simple plain bearing pad against which the upper portion of the joint ball of the humerus bears. Kinnett appears to indicate that the distal or outer end of the clavicle would be immovably affixed to the acromion by means of his acromion prosthesis, which would greatly limit certain motions of the shoulder. Kinnett does not disclose any form of articulated joint between the clavicle and acromion extension of the scapula, as provided by the present acromioclavicular joint prosthesis.

U.S. Pat. No. 5,944,757 issued on Aug. 31, 1999 to Paul M. Grammont, titled "Total Trochitero-Acromial Shoulder Prosthesis," describes a shoulder joint prosthesis comprising an artificial ball for attachment to the shoulder joint end of the humerus and a plain bearing for attachment to the lower surface of the acromion, against which the ball of the humerus bears. However, Grammont fails to provide any form of attachment between the acromion and the clavicle. The present acromioclavicular joint prosthesis provides for an articulated connection between these two skeletal components.

U.S. Pat. No. 6,132,467 issued on Oct. 17, 2000 to Arnold Keller, titled "Endoprosthesis, In Particular For The Sternoclavicular Joint," describes a prosthetic joint configured for installation in a joint where the two bones cannot be easily distracted (separated) from one another. One such joint is the inner end of the clavicle and its connection to the sternum, which is the opposite end of the clavicle from the end to which the present acromioclavicular prosthesis is secured. While Keller does provide a ball joint, he does not disclose the means for positively attaching the two bones together, particularly the acromion and scapula, as provided by the present invention.

U.S. Pat. No. 6,193,758 issued on Feb. 27, 2001 to Randall J. Huebner, titled "Shoulder Prosthesis," describes a replacement for the shoulder contact ball of the humerus. The Huebner prosthesis includes an extension which is driven into the medullar (marrow) canal of the humerus, to secure the joint ball in place. However, Huebner does not disclose any form of joint prosthesis for connecting the acromion and clavicle together, as provided by the present invention.

U.S. Pat. No. 6,620,197 issued on Sep. 16, 2003 to Brian J. Maroney et al., titled "Method And Apparatus For Performing A Shoulder Replacement Procedure In The Treatment Of Cuff Tear Arthropathy," describes a prosthetic humerus ball joint, similar to the Huebner device discussed immediately above. The major difference between the Huebner and Maroney et al. prostheses is that Maroney et al. provide a spherical ball surface of more than 180 degrees of spherical arc. However, no prosthetic acromioclavicular joint is disclosed by Maroney et al.

U.S. patent Publication No. 2002/99,381 published on Jul. 25, 2002, titled "Method And Apparatus For Resecting A Greater Tubercule From A Humerus Of A Patient During Performance Of A Shoulder Replacement Procedure," describes a tool and method for removing the protuberance of bone from the humerus which is adjacent the ball end thereof. This tool and method would be used during the operation for installing the prosthetic ball described in the '197 U.S. patent to Maroney et al., described immediately above. No acromioclavicular joint prosthesis is disclosed in the '381 patent Publication.

U.S. patent Publication No. 2002/99,445 published on Jul. 25, 2002, titled "Method And Apparatus For Performing A Shoulder Replacement Procedure In The Treatment Of Cuff Tear Arthropathy," is the earlier publication of the U.S. patent application which resulted in the issuance of the '197 U.S. patent to Maroney et al. on Sep. 16, 2003, discussed further above. The same points of difference between the device of the Maroney et al. '197 U.S. patent and the present invention noted in that discussion, are seen to apply here as well.

U.S. patent Publication No. 2003/144,738 published on Jul. 31, 2003, titled "Acromial-Humeral Prosthesis And Method Of Implantation," describes a two piece bearing which is affixed to the underside of the acromion extension of the scapula, and which serves as a plain bearing surface for the upper portion of the ball of the humerus. However, the '738 publication does not disclose any form of connection between the acromion and the clavicle, which connection is addressed by the present prosthetic joint invention.

U.S. Design Pat. No. 285,969 issued on Sep. 30, 1986 to James G. Kinnett, titled "Acromial Prosthesis Component For Total Shoulder Prosthesis System," illustrates a design for the acromion attachment bearing described in the '450 U.S. Utility patent to the same inventor, discussed further above. As in the case of his '450 U.S. Utility patent, no acromioclavicular prosthetic joint is disclosed by Kinnett in his '969 U.S. Design patent.

French Patent Publication No. 2,541,890 published on Sep. 7, 1984, titled "Total Shoulder Prosthesis," describes (according to the drawings and English abstract) a prosthetic humerus ball joint replacement and a prosthetic replacement for the glenoid socket of the scapula. The glenoid replacement also attaches beneath the acromion, but no acromioclavicular joint prosthesis is disclosed in the '890 French Patent Publication. While the inventor named in the '890 French patent is also the inventor of record in the '757 U.S. patent discussed above, it should be noted that the inventions described in the '757 U.S. patent and the '890 French Patent Publication are different from one another.

Finally, PCT Patent Publication No. WO 93/09733 published on May 27, 1993, titled "Modular Prosthesis," describes a series of components for a modular humerus ball joint prosthesis. The assembly is quite similar to that disclosed in the Huebner '758 and Maroney et al. '197 U.S. patents and the Maroney et al. '445 U.S. patent Publication. The same points of difference noted further above in the discussion of the '758 Huebner and '197 Maroney et al. U.S. patents and the Maroney et al. '445 U.S. patent Publication are seen to apply here as well, i.e. no acromioclavicular joint prosthesis is disclosed in those patents and patent publication.

None of the above inventions and patents, taken either singly or in combination, is seen to describe the instant invention as claimed. Thus an acromioclavicular joint prosthesis solving the aforementioned problems is desired.

SUMMARY OF THE INVENTION

The present acromioclavicular joint prosthesis provides a device for replacing the joint between the acromion extension of the scapula and the distal or outward end of the clavicle. This joint can become separated due to excessive force being applied thereto and resultant tearing of the ligaments or tendons securing the two bones together. Alternatively, the joint may deteriorate due to arthritis or other disease. Regardless of the underlying reason, a damaged or separated acromioclavicular joint requires repair or replacement.

The present invention serves as a durable and flexible prosthetic replacement for the acromioclavicular joint in the human skeletal structure. The present prosthesis includes an acromion attachment component and a clavicle attachment component, with the two bone attachment components being linked by a spring loaded spherical joint, or other joint providing two degrees of freedom of motion. A "breakaway" joint connection may be provided between the two components, with the "breakaway" connection allowing the prosthesis to temporarily "break" linearly when excessive force is applied thereto. Such a joint may be realigned fairly quickly and easily by a medical professional, if misalignment occurs.

Each bone attachment component of the present invention also includes an extension providing positive attachment to the respective bone structures. Passages and other components are provided for new bone growth to develop therethrough and therearound, thereby further strengthening the prosthetic installation. The present invention further includes tools providing for the installation of the present acromioclavicular prosthesis, and a method of surgically installing the prosthesis for replacement of the acromioclavicular joint.

Accordingly, it is a principal object of the invention to provide an acromioclavicular joint prosthesis for prosthetic replacement of a natural acromioclavicular joint in the human skeletal structure.

It is another object of the invention to provide a prosthesis having an acromion attachment component and a clavicle attachment component, with the two components being connected by an articulated joint.

It is a further object of the invention to provide an acromioclavicular joint prosthesis having extensions of both the acromion and clavicle attachment components, with the extensions providing additional security for the attachment by means of bone growth and adhesion thereto.

Still another object of the invention is to provide tools for the installation of the present acromioclavicular joint prosthesis, as well as a method for installing the prosthesis.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
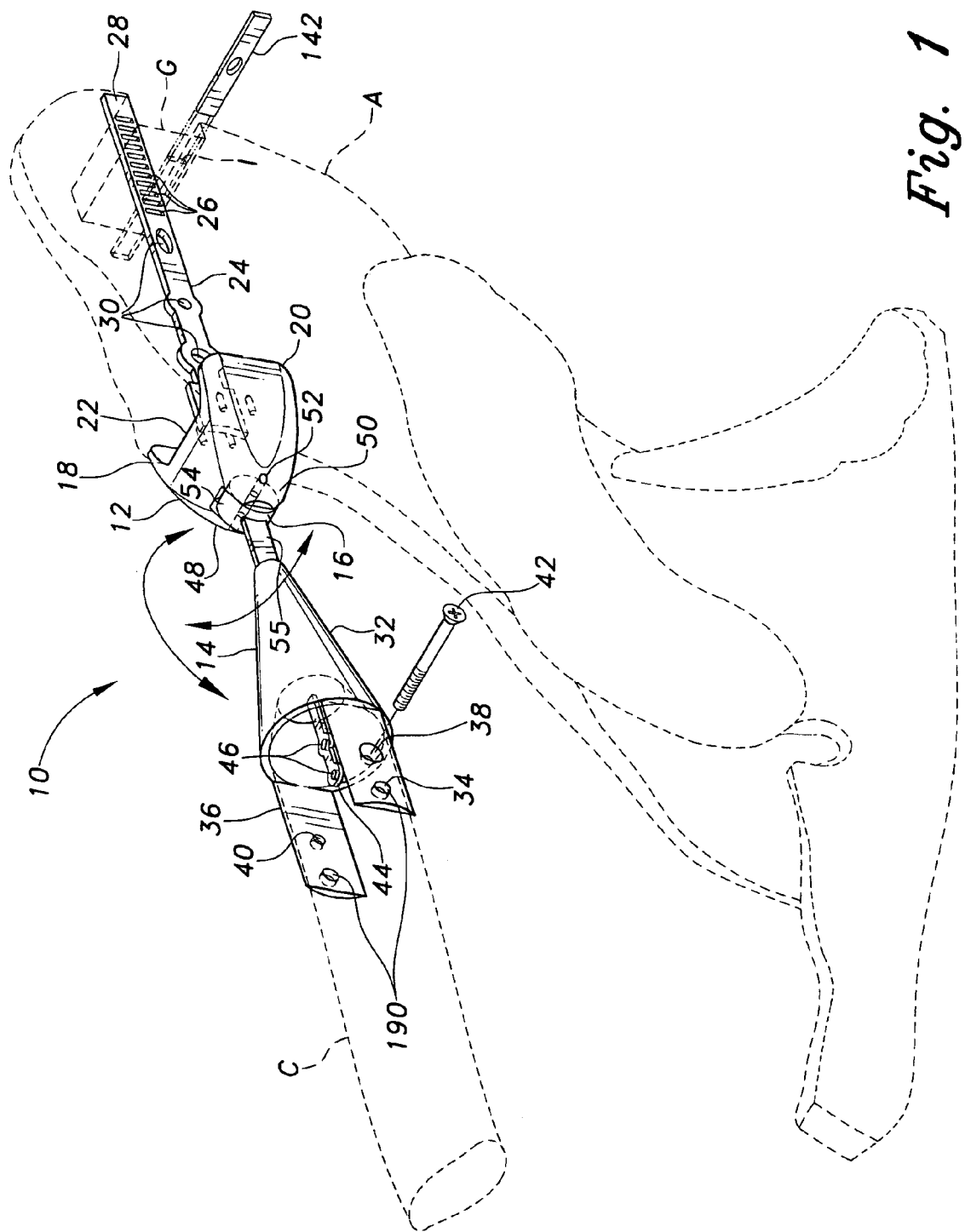
FIG. 1 is a perspective view of a first embodiment of a left side acromioclavicular joint prosthesis of the present invention as seen from the front and top, showing various features thereof.

The present invention comprises a series of embodiments of an acromioclavicular joint prosthesis, serving to reconnect a separated or damaged joint between the acromion of the scapula and the clavicle. FIG. 1 of the drawings provides a front and top perspective view of a first embodiment of the present prosthesis, designated by the reference numeral 10. The prosthesis 10 of FIG. 1 is relatively simple in comparison to other embodiments of the present invention, having only a single pivot point or hinge between the two attachment components to permit only one degree of freedom of motion between the two components. It will be seen that additional motion may be provided by including additional pivotal axes and/or telescoping mechanisms, as may be required or desired.

The acromioclavicular prosthesis 10 of FIG. 1 essentially comprises an acromion attachment component 12, a clavicle attachment component 14, and an articulated linkage 16 therebetween to connect the two components 12 and 14 to one another. The prosthesis 10 is shown diagrammatically attached to the left shoulder in FIG. 1, the clavicle being designated at C, the acromion process at A, the coracoid process at CP, the glenoid cavity at GC, the scapular notch at SN, and the remainder of the scapula S being fragmented. The acromion process A is reshaped as required to fit the acromion attachment component 12 closely and to provide a solid attachment for the component 12. The clavicle C is also reshaped as required to provide a good fit for its clavicle attachment component 14.

The acromion attachment component 12 includes a pair of opposed short flanges 18 and 20 which straddle the edge of the acromion A, with the flanges 18 and 20 sandwiching a rounded seat 22 therebetween (the equivalent seat is more clearly shown in the alternate embodiment device illustrated in subsequent drawings). A single thin, flat, elongate acromion attachment and locking band 24 extends axially from the seat 22, opposite the linkage 16. The band 24 includes a series of tool gripping slots 26 formed through its free distal end 28 and one or more apertures 30 therethrough which provide for bone growth therethrough during the healing process to anchor the component 12 more solidly to the acromion A. The attachment and locking band 24 is used to pull the acromion attachment component 12 tightly against the reshaped acromion A, using a tool and method described in detail further below. The acromion attachment component 12 also includes a series of small anchoring spikes which extend from the seat 22, with the spikes more clearly shown in alternate embodiments in subsequent drawings.

The clavicle attachment component 14 of FIG. 1 comprises a generally cylindrical or conical body portion 32 having a pair of opposed, generally parallel clavicle attachment arms 34 and 36 extending therefrom, opposite the articulated link 16 joining the two bone attachment components 12 and 14. The first clavicle arm 34 includes a countersunk hole 38 therethrough, and the opposite clavicle arm 36 includes a threaded passage 40 therethrough for the installation of a screw 42 which passes through a passage which is drilled through the clavicle C during the installation operation. A clavicle insertion and locking band 44 extends axially from the clavicle attachment body 32, between the two attachment arms 34 and 36. The clavicle band 44 inserts in an axial slot which is formed in the attachment end of the clavicle C, with the band 44 also including one or more bone growth apertures 46 therein to provide more solid attachment for the clavicle component 14 once the installation has healed.

The articulated link 16 joining the acromion and clavicle components 12 and 14 of the prosthesis 10 of FIG. 1 comprises a simple hinged joint, with an optional leaf spring providing for articulation normal to the hinge axis. The acromion component 12 includes a bifurcated pair of joint attachment arms 48 and 50 extending therefrom, with a transverse hinge pin 52 extending across the two arms 48 and 50. The attached clavicle component 14 includes an attachment fitting 54 having a lateral passage therethrough, through which the hinge pin 52 passes to pivotally link the two components 12 and 14 together. A leaf spring 55 may extend between the attachment fitting 54 and the clavicle attachment body 32, with its thinnest dimension normal to the axis of the pivot pin 52 in order to provide joint articulation in two mutually normal planes. Other means of linking the components 12 and 14 may be provided, as exemplified in other embodiments illustrated in subsequent drawings and discussed below.

Figure 2:
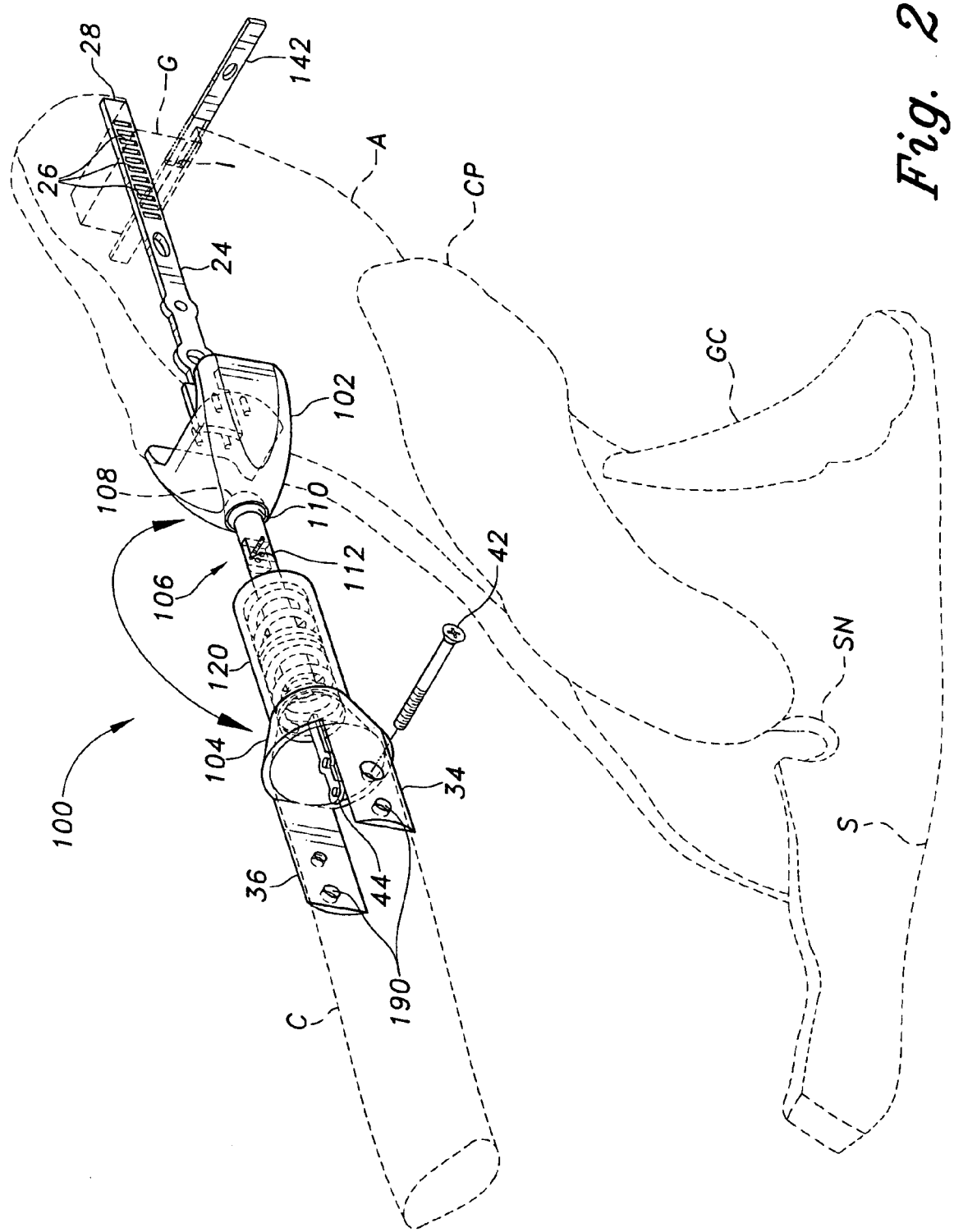
FIG. 2 is a perspective view of an alternative embodiment of the acromioclavicular joint prosthesis of the present invention as seen from the front and top, showing an alternative connection assembly.

FIG. 2 of the drawings provides an illustration of an alternative acromioclavicular joint prosthesis, designated by the reference numeral 100. The prosthesis 100 includes an acromion attachment component 102, opposite clavicle attachment component 104, and a joint structure 106 between the two components 102 and 104, essentially as in the prosthesis 10 of FIG. 1. However, the joint assembly 106 of the prosthesis 100 is somewhat more complex than the simple hinged or pivoting joint 16 of the prosthesis 10 of FIG. 1 and provides additional degrees of freedom of motion, which may be desirable in some patients receiving the present acromioclavicular prosthesis.

While most of the various components of the two attachment components 102 and 104 are identical to the corresponding components of the prosthesis 10 of FIG. 1, e.g. the acromion attachment and locking band 24, the opposite clavicle attachment and locking band 44, the clavicle attachment arms 34 and 36, etc., it will be seen that the joint structure between the two attachment components 102 and 104 is quite different from the simple hinged joint 16 of the prosthesis 10 of FIG. 1. The prosthesis 100 of FIG. 2 includes a spherical joint 106, formed by a spherical socket 108 in the acromion attachment component and a mating ball 110 extending from the clavicle attachment component 104, thereby providing three degrees of angular freedom of motion. It will be seen that the ball and socket relationship may be reversed if so desired, with the ball extending from the acromion attachment component and the socket formed in the extended end of the clavicle attachment component, if so desired.

Figure 3:
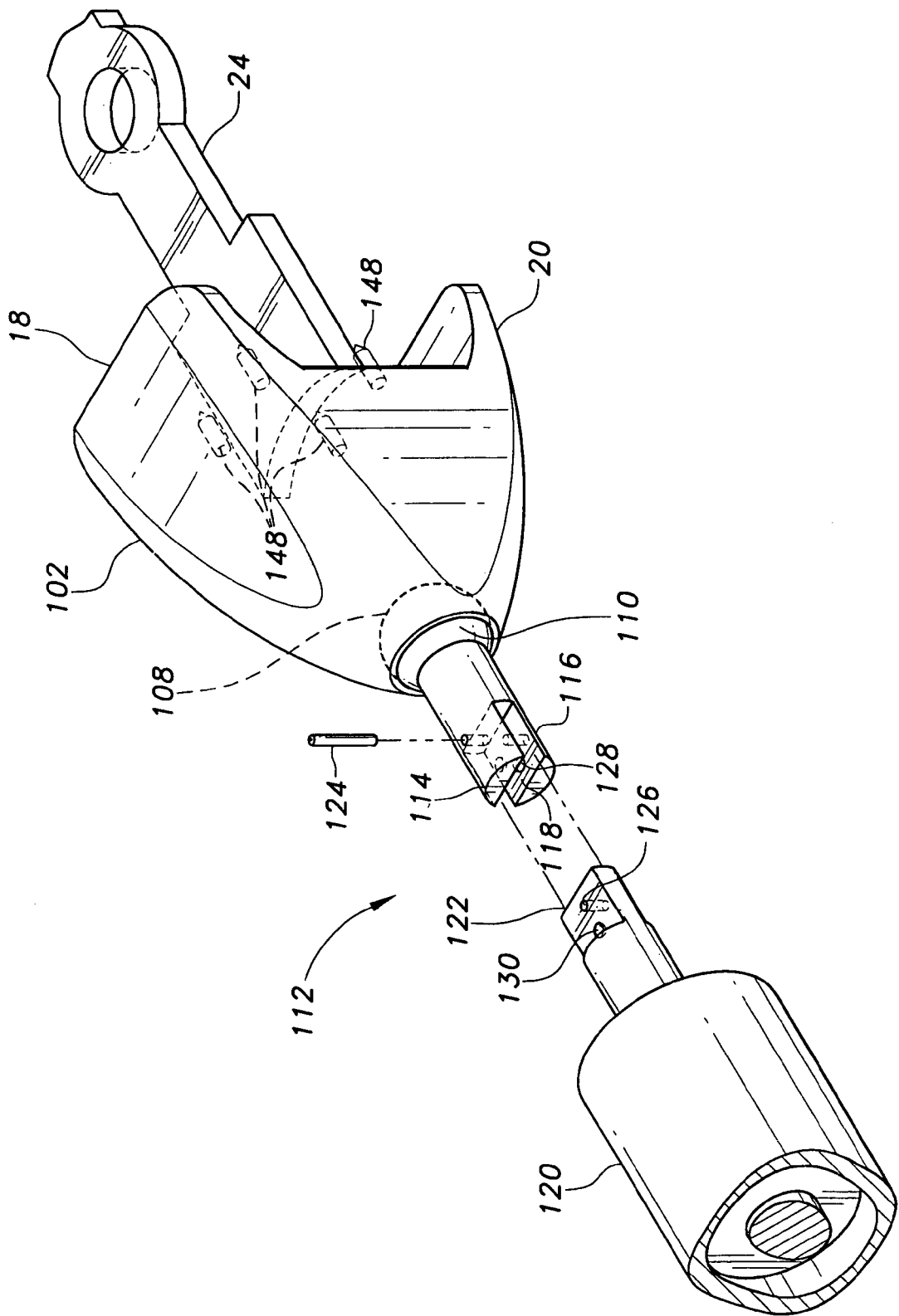
FIG. 3 is a detailed, exploded perspective view of the alternative breakaway connection between the acromion and clavicle components, showing various details of the connection.
Figure 4:
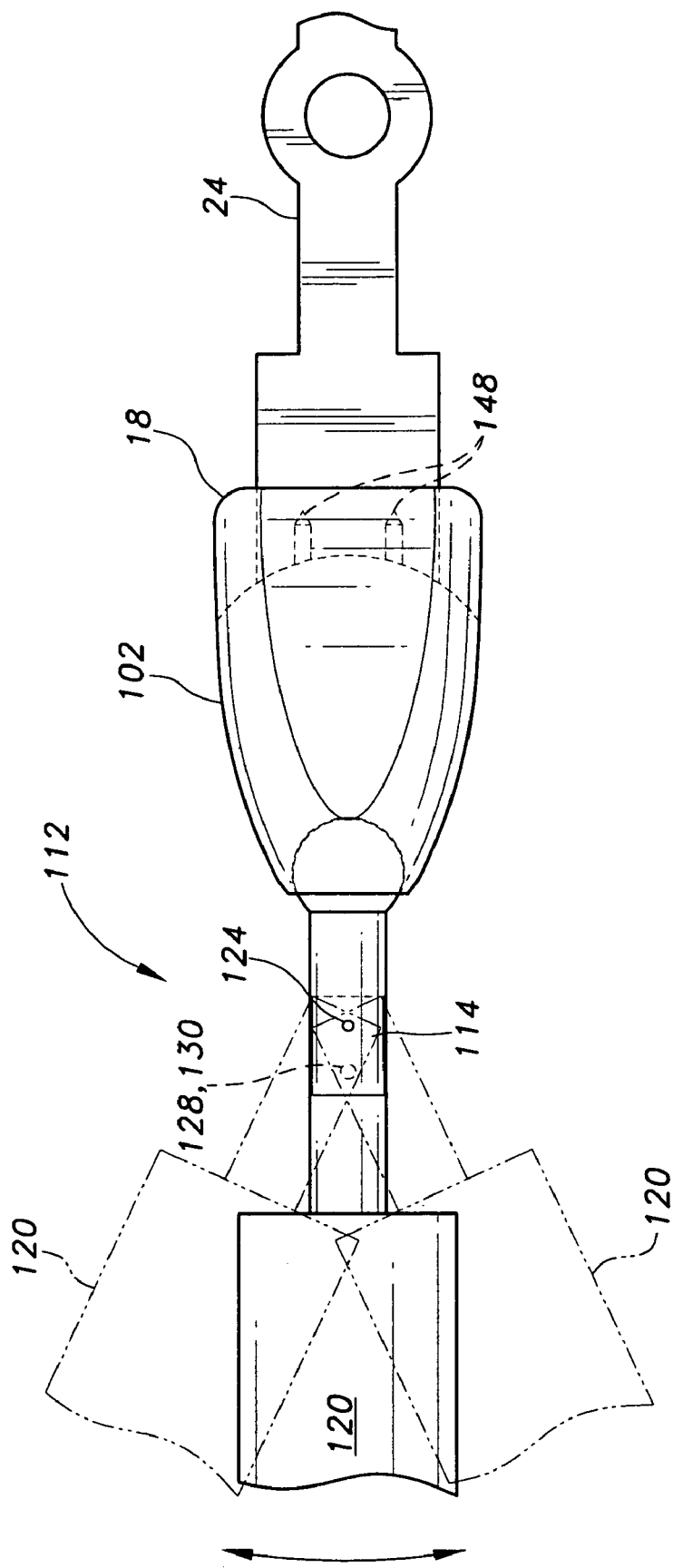
FIG. 4 is a front elevation view of the alternative embodiment breakaway connection, showing its operation.

An additional angularly displaceable, locking "breakaway" joint component 112 may be provided between the spherical joint 106, if so desired. FIGS. 3 and 4 respectively provide exploded perspective and front elevation views of this "breakaway" joint 112. The joint 112 includes a pair of arms 114 and 116 extending from the ball fitting 110 which is secured to the acromion attachment component 102, with the two arms 114 and 116 forming a bifurcated fork with a slot 118 between the two arms 114 and 116. The opposite joint component extending from the clavicle attachment shock absorber body 120 includes a tongue 122, which fits within the slot 118 between the two attachment arms 114 and 116 of the opposite joint member. A pin 124 is permanently installed and passes laterally through the attachment arms 114 and 116, and through a passage 126 through the tongue 122 to allow the tongue to pivot relative to the fork arms 114 and 116.

Spring-loaded retaining balls 128 protrude resiliently from the mutually facing inner surfaces of the two arms 114 and 116, and engage corresponding dimples or depressions 130 formed in the opposite surfaces of the tongue 122. The retaining balls 128 protrude into the dimples 130 to hold the arms 114, 116 and tongue 122 in linear alignment with one another, unless a high force is encountered which causes the assembly to dislodge or break away from its locked linear arrangement and pivot about the pin 124. This dislocation of the angularly displaceable "breakaway" joint assembly 112 acts to prevent damage to other components of the prosthesis, and may be reset by a medical professional without undue difficulty.

Figure 5:
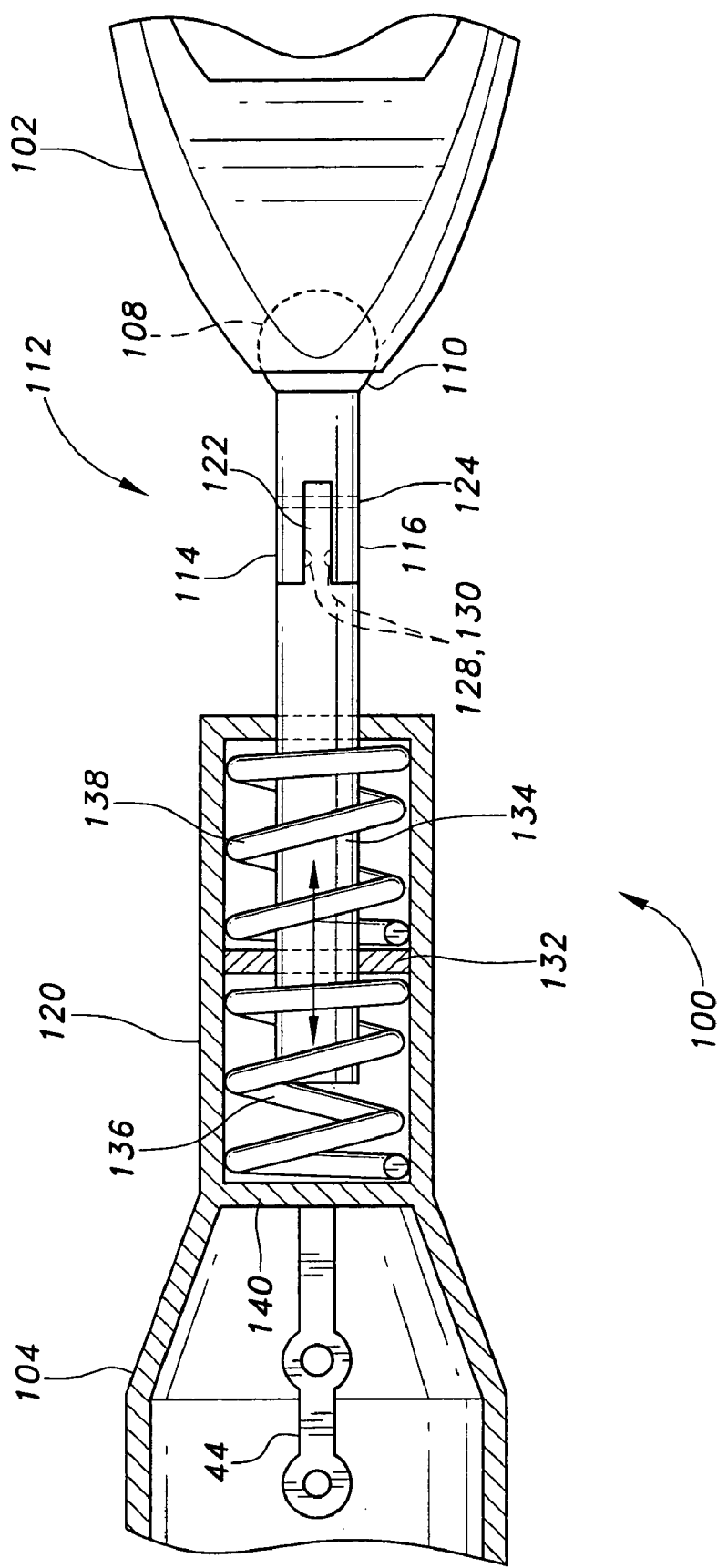
FIG. 5 is a top plan view in partial section of an alternative embodiment shock absorption component of the present prosthetic device, showing details thereof.

FIG. 5 provides a detailed top plan view in partial section of another resilient joint component for incorporation with the present acromioclavicular joint prosthesis, if so desired. A person having the present acromioclavicular prosthesis may occasionally encounter a sharp compressive blow to the shoulder, which could result in damage to the prosthesis. Accordingly, a linearly displaceable, spring-loaded fitting may be provided in the acromion attachment shock absorber body 120 of the prosthesis embodiment 100, if so desired. The component 120 acts somewhat as a shock absorber, as the name implies. A washer 132 or the like is immovably affixed to the shaft extension 134 which carries the tongue 122 of the breakaway fitting 112. Compression and extension springs 136 and 138 are assembled within the housing or body 120 on opposite sides of the washer 132.

A compression of the prosthetic joint 100 will cause the compression spring 136 to compress between the washer 132 and the opposite attachment end 140 of the shock absorber body 120 of the clavicle attachment component 104, with the compression spring 136 rebounding to return the clavicle attachment component 104 to its original position relative to the acromion component 102, once the compressive force is removed. A tensile force applied to the joint results in the compression of the extension spring 138 between the washer 132 and the distal end 142 of the shock absorber body 120. Again, the assembly returns to a neutral point once the tensile force is removed. The various joint assemblies illustrated in the prosthesis embodiment 100 may be used separately or in combination with one another, as desired.

Figure 6:
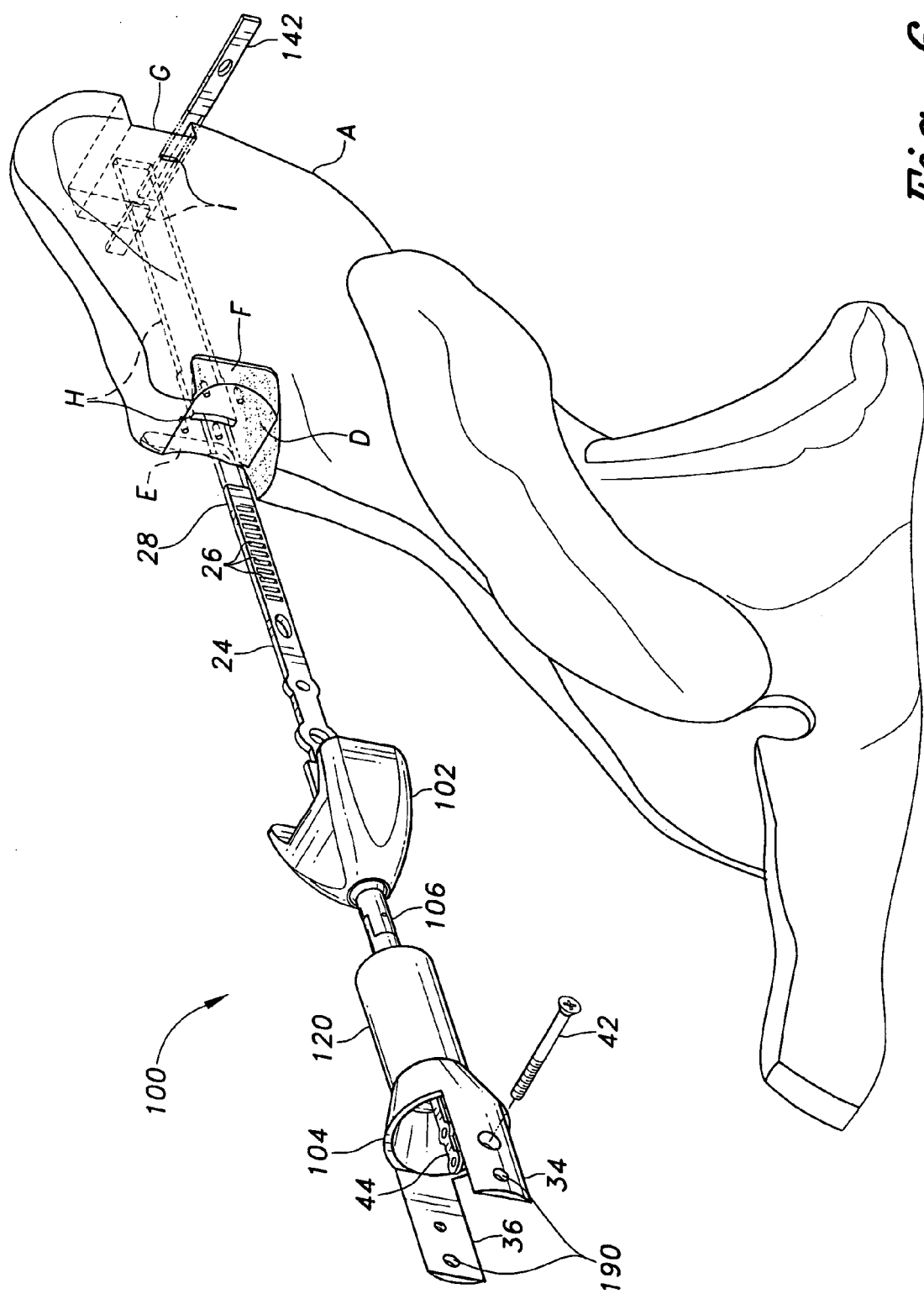
FIG. 6 is an exploded perspective view as seen from the front and top showing the initial steps in installing the present acromioclavicular joint prosthesis to the acromion of the scapula.
Figure 7:
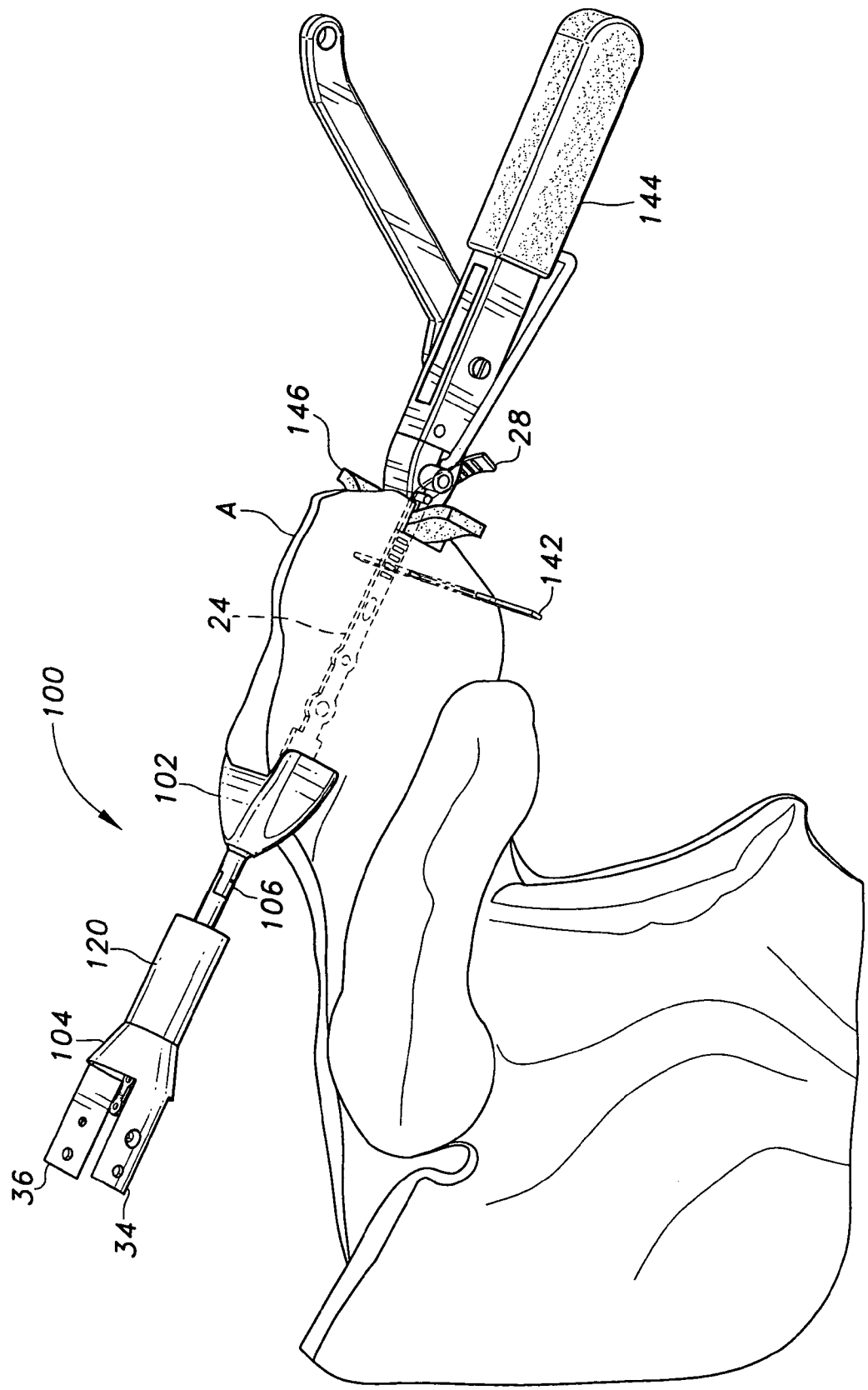
FIG. 7 is a perspective view as seen from the front and top showing subsequent steps in securing the present acromioclavicular joint prosthesis in the acromion, and an exemplary installation tool.
Figure 8:
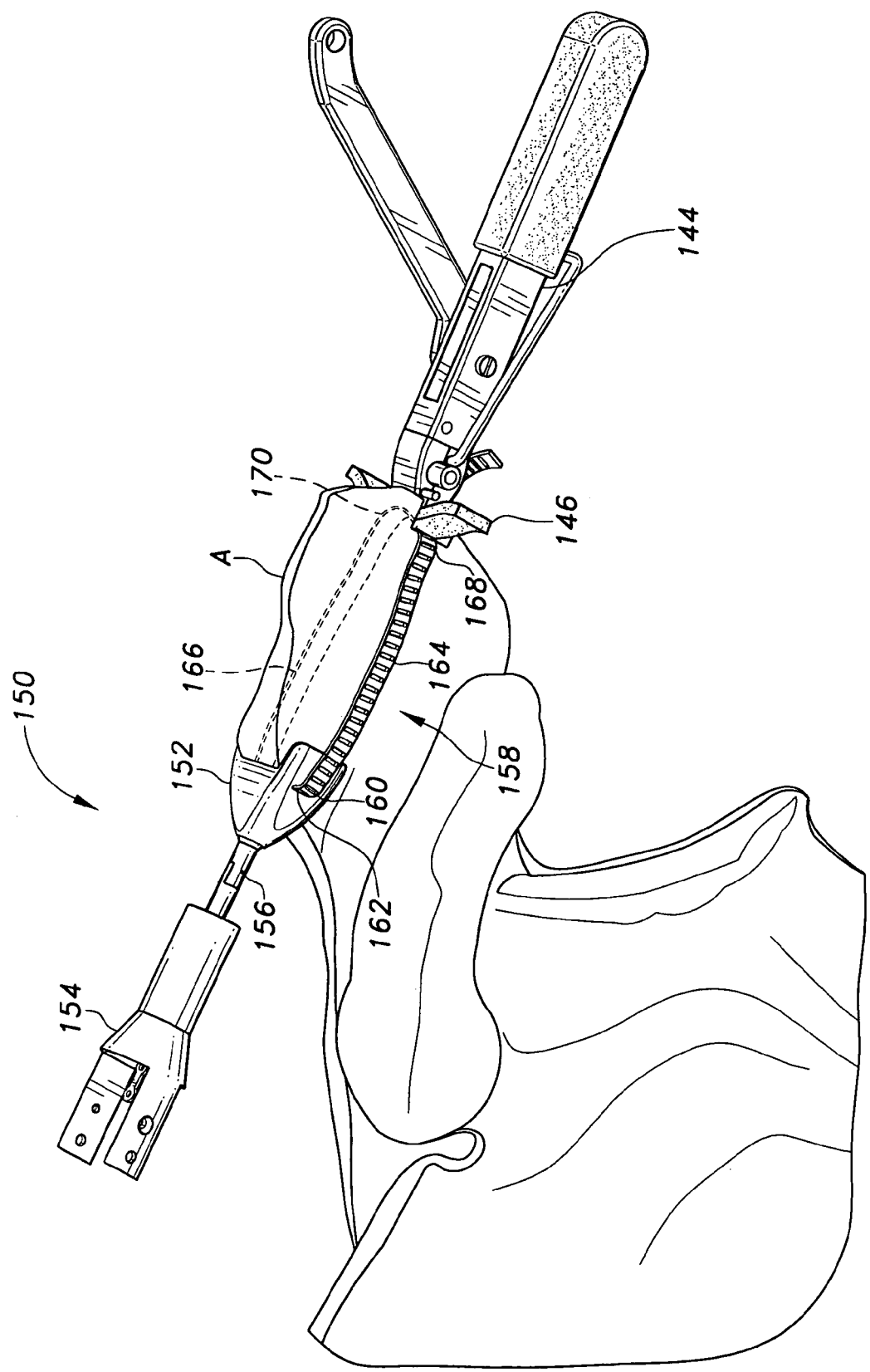
FIG. 8 is a perspective view of an alternative embodiment securing means as seen from the front and top, using the tool of FIG. 7 and a generally circumferential locking band around the acromion.
Figure 9:
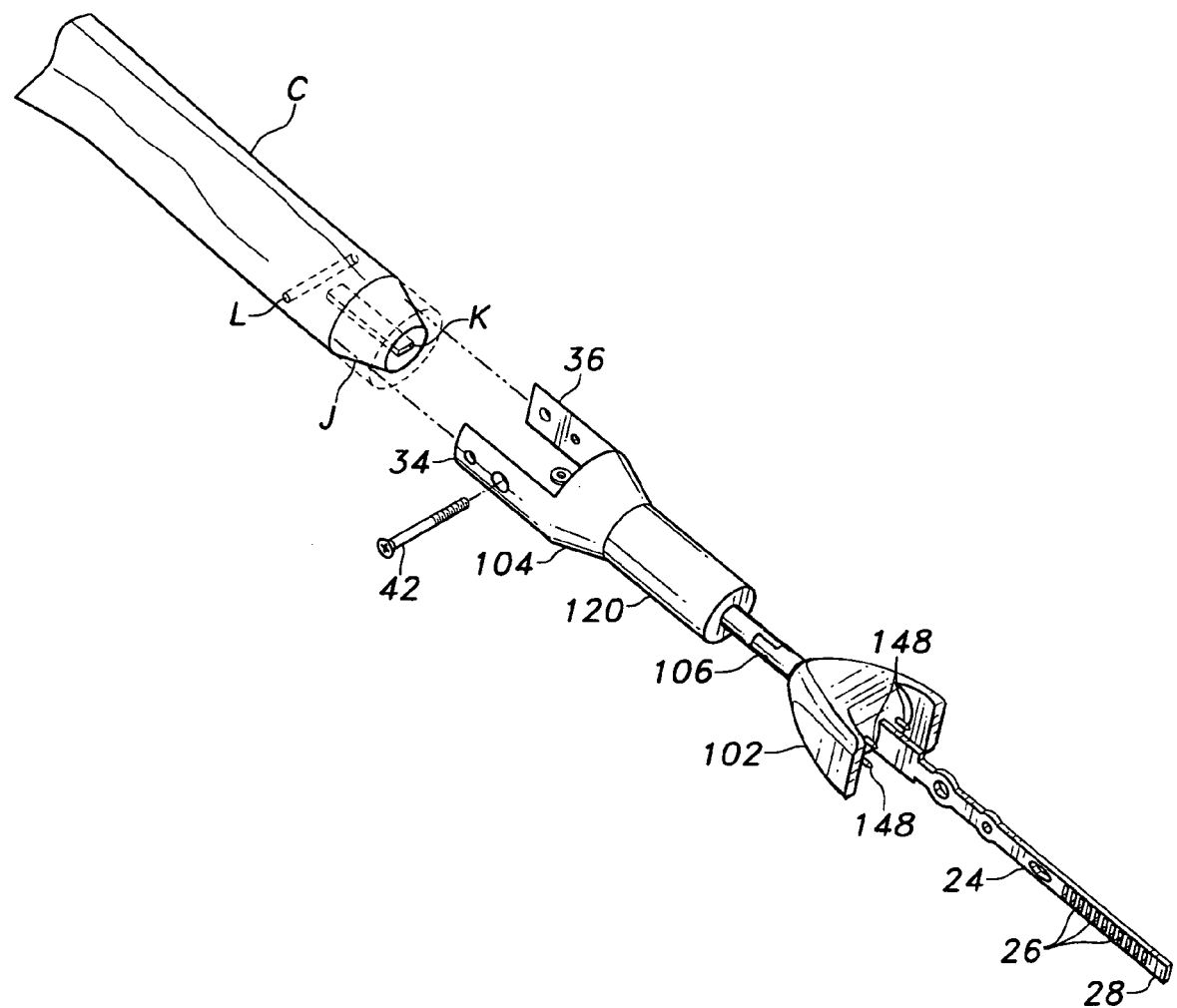
FIG. 9 is an exploded perspective view as seen from the front and top showing the initial steps in installing the present acromioclavicular joint prosthesis to the distal end of the clavicle.
Figure 10:
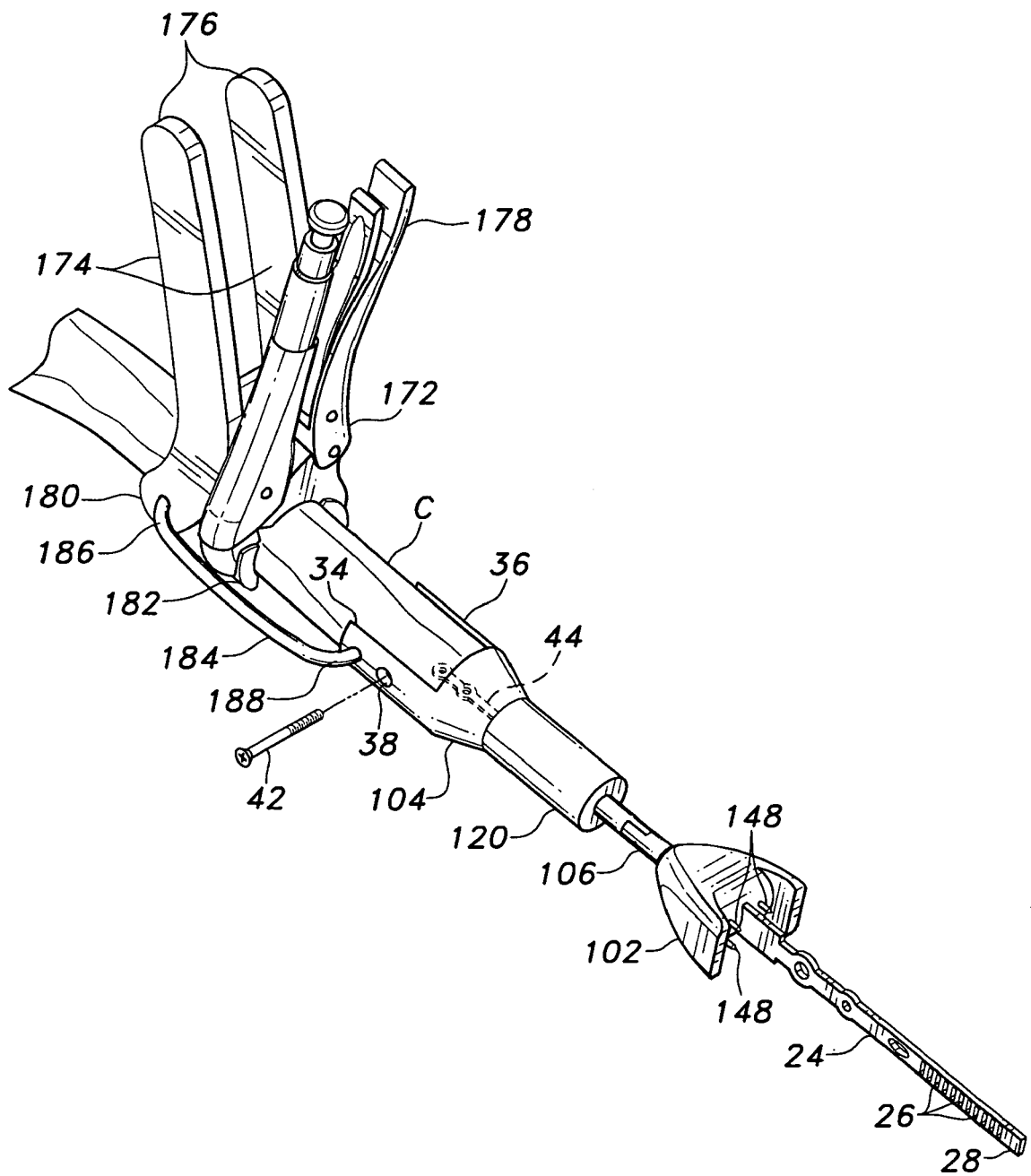
FIG. 10 is a perspective view as seen from the front and top showing a subsequent step in the installation of the present prosthesis to the clavicle, and an exemplary installation tool.
Figure 11:
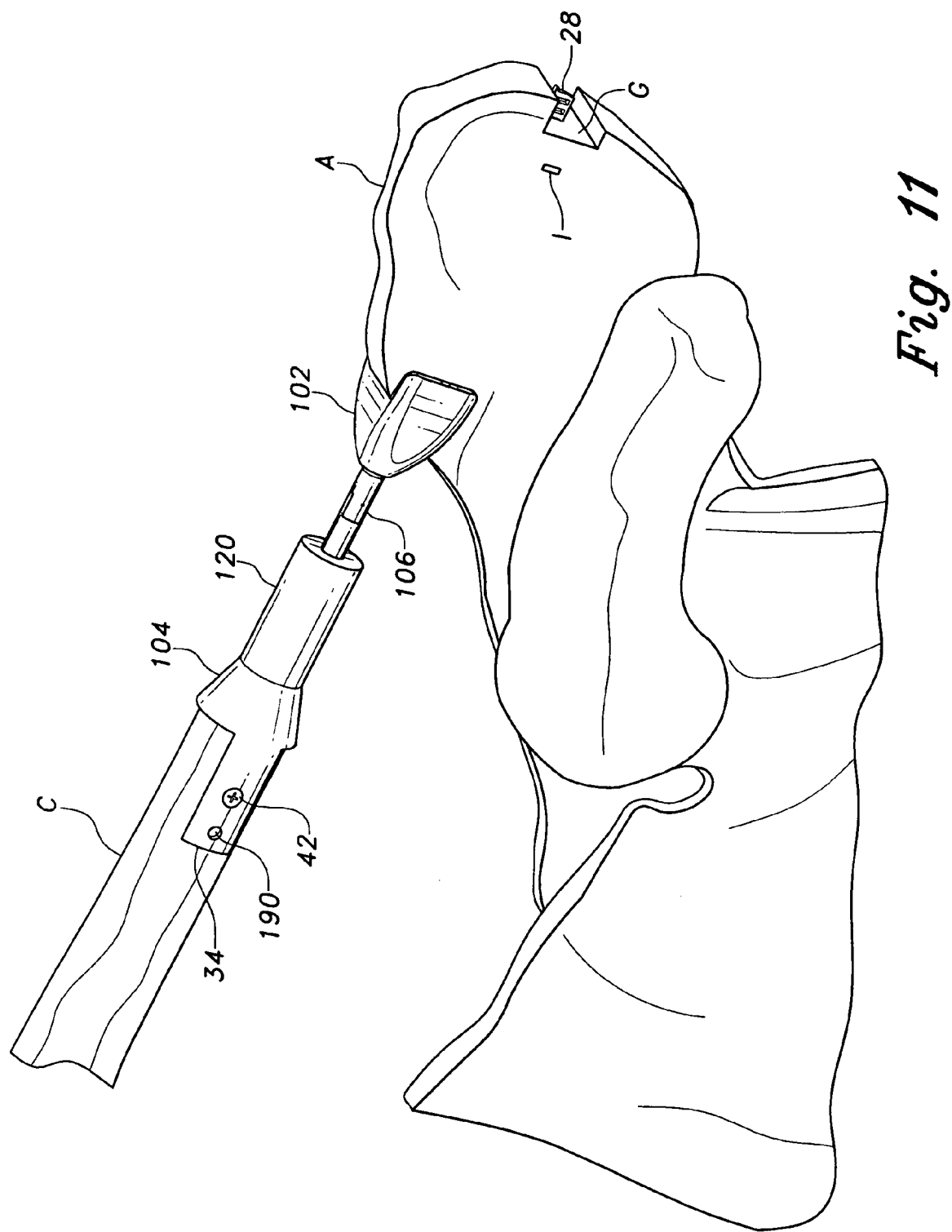
FIG. 11 is a perspective view as seen from the front and top showing the completed installation of the present acromioclavicular joint prosthesis between the distal end of the clavicle and acromion.

FIGS. 6 through 10 illustrate the installation of the present acromioclavicular prosthesis between the acromion and clavicle, with FIG. 8 illustrating yet another alternative embodiment and FIG. 11 illustrating the completed installation. The embodiment illustrated in FIGS. 6, 7, and 9 through 11 is the prosthesis 100 shown in FIG. 2, with details thereof being illustrated in FIGS. 3 through 5. The embodiment of FIG. 8 differs in its means of anchoring or locking to the acromion, and is discussed in detail further below.

FIG. 6 illustrates the initial steps in the method of attaching the acromioclavicular prosthesis 100 to the acromion A. Initially, the acromion A must be reshaped in order to accommodate the acromion attachment component 102. This is accomplished by forming a series of cuts, depressions, slots, and/or receptacles in the acromion A using conventional surgical tools and methods. While a certain order is described below, it will be recognized that the specific order of forming the cuts and receptacles in the acromion A will depend upon many factors, such as the tools used, the specific joint structure of the patient, and perhaps other factors as well. The specific order described below is not a required condition for the installation of any of the embodiments of the acromioclavicular joint prosthesis of the present invention. It will also be appreciated that while the embodiment 100 of the present acromioclavicular prosthesis is illustrated in FIGS. 6, 7, and 9 through 11, the installation method described herein is generally applicable to any of the embodiments of the present invention.

Initially, the surgeon may cut away the site where ligaments originally attached the clavicle to the acromion A to form an acromion attachment component seat D. Additional reshaping of the acromion attachment component seat is carried out by forming a pair of shallow opposed recesses E and F to each side of the acromion A in order to seat the two opposed flanges 18 and 20 of the acromion attachment component 102 (or 12, etc.). The acromion attachment component 102 may obviously be manufactured in a wide range of sizes and thickness, in order for the thickness of the device to closely match the thickness of the acromion so that the outer flanges 18 and 20 lie essentially flush with the surface of the acromion A when the prosthesis 100 is completely installed.

The surgeon may next form a generally rectangular recess G in the opposite, outboard or distal edge of the acromion A, to accommodate the distal end 28 of the locking band 24 and the operation of an attachment tool, as illustrated in FIGS. 7 and 8 and discussed further below. A passage H is then formed through the acromion A, connecting the acromion attachment component seat D and the opposite locking band and tool recess G. The passage H may have a relatively low and wide cross section, just sufficient to accept the width and thickness of the acromion attachment and locking band 24 therethrough. Finally, a transverse passage I is formed through the acromion A, intersecting the locking band passage H. This passage I provides for the installation of a locking clip 142 across the locking band passage H, with the clip 142 passing through one of the tool grip slots 26 in the band 24 to prevent the band 24 from slipping out of the passage H.

At this point, the attachment end of the clavicle C may be reshaped as required. The clavicle attachment component 104 (or 14, etc.) includes a generally conical socket defined by the shape of the clavicle attachment component. The attachment end of the clavicle C is reshaped accordingly by removing bone material to form a congruent shape J for the end of the clavicle C, generally as shown in FIG. 9. A relatively wide and shallow slot K is then formed axially in the attachment end of the clavicle C, to accept the clavicle insertion and locking band 44. Finally, a hole or passage L is formed transversely through the clavicle C, for the clavicle attachment screw 42 which passes through the two clavicle attachment component arms 34 and 36 to secure them to the end of the clavicle C.

Once the acromion A has been reshaped as required, the acromion attachment component 102 (or 12, etc.) may be secured to the acromion A by inserting the acromion component attachment and locking band 24 through the acromion slot H until the acromion attachment component seat 22 is seated within the mating recess D previously formed in the acromion A. A tensioning tool 144 (essentially similar to conventional tools used to tension packaging bands and straps, but formed of surgical grade materials) is applied to the distal end 28 of the locking band 24 and used to pull the band 24 in order to draw the acromion attachment component 102 tightly against the acromion A, generally as shown in FIG. 7 of the drawings. A resilient pad or cushion 146 may be applied between the acromion bone A and the nose of the tool 144 in order to avoid chipping the acromion during this process.

It will be noted that the acromion attachment component 102 includes a series of small spikes 148 extending from the seat 22 thereof. These spikes 148 are shown most clearly in FIGS. 3, 4, 9, and 10 of the drawings. As the acromion attachment component 102 is drawn tightly against the seat D previously cut into the acromion bone A, the spikes 148 imbed themselves in the acromion bone A, thereby further securing the attachment component 102 to the acromion A. A conventional bone adhesive or cement may be used to further enhance the attachment of the acromion attachment component 102 (or other embodiment) to the acromion bone A, as desired or required by the surgery. The locking clip 142 is inserted through its transverse passage I in the acromion A and through one of the slots 26 in the attachment and locking band 24, to preclude withdrawal of the locking band 24 from its passage H through the acromion A.

When the above described attachment of the acromion attachment component 102 (or other) has been completed, any excessive material of the locking band 24 may be trimmed off to leave only a short stub extending from the tool recess G previously formed in the acromion A, generally as shown in the completed installation shown in FIG. 11. As the surgery heals, the acromion bone material will regrow around the end of the locking band 24 and through the bone growth passages 30 in the locking band 24, thereby further anchoring the acromion attachment component 102 (or other) solidly, permanently, and immovably to the acromion bone A.

FIG. 8 of the drawings illustrates a further embodiment of the present acromioclavicular prosthesis, designated by the reference numeral 150. In this embodiment, the acromion attachment component 152 does not have the acromion attachment and locking band extending axially therefrom, as do the other embodiments of FIGS. 1 through 7 and 9 through 11. The acromioclavicular joint prosthesis 150 of FIG. 8 instead has an attachment and locking band which surrounds the acromion A when installed. The clavicle attachment component 154 and the connecting linkage assembly 156 of the prosthesis 150 remain essentially the same as in the embodiments illustrated in FIGS. 2 through 7 and 9 through 11, with the simplified alternative linkage illustrated for the prosthesis embodiment of FIG. 1 also being adaptable to the prosthesis 150 of FIG. 8, if so desired.

In the prosthesis 150 of FIG. 8, the acromion attachment and locking band 158 comprises an elongate band which has its central portion 160 passing through a transverse slot 162 formed through the acromion attachment component 152. The two extended portions 164 and 166 pass to each side of the acromion A and meet at the distal portion of the acromion A opposite the acromion attachment component 152, thereby surrounding the acromion A. The two ends 168 and 170 of the band 158 are gripped by a banding tool 144, similar to the tool 144 illustrated in FIG. 7, and pulled taut around the acromion A and secured by a conventional banding clip to hold the prosthesis 150 in place on the acromion A. This installation method eliminates the need for forming the passages H and I through the acromion A, thereby simplifying the process.

The reshaping of the clavicle C has been described further above, and once the clavicle reshaping has been accomplished, the clavicle attachment component 104 (or other embodiment) may be installed on the clavicle C. This installation is illustrated in FIGS. 9 and 10 of the drawings. Initially, the clavicle attachment component 104 is placed over the reshaped end of the clavicle C, with the two clavicle attachment arms 34 and 36 straddling the end of the clavicle C and the axially extending clavicle insertion and locking band 44 inserted into the corresponding axial passage K previously formed in the clavicle C. A conventional bone adhesive or cement may be applied to provide a more secure attachment, if so desired.

At this point, the clavicle attachment component 104 must be pulled tightly up against the end of the clavicle C in order to assure a secure installation. The present invention may include a specialized tool 172 which may be temporarily clamped to the clavicle C, and used to pull the clavicle attachment component 104 tightly against the end of the clavicle C. Padding, not shown, is preferably placed between the clavicle C and the tool jaws to avoid bone damage. The clavicle attachment tool 172 may generally be in the form of a pair of Vise-Grip® pliers, or other suitable hands-free clamp which may be temporarily secured to the clavicle C. However, the tool 172 further includes a pair of levers 174 extending laterally therefrom, with the levers 174 having hand grip ends 176 adjacent the hand grip end 178 of the attachment tool 172 and opposite tensile force application ends 180 adjacent the jaws 182 of the gripping tool 172.

A tension rod 184 extends from the tensile force application end 180 of each of the levers 174; only a single one of the tension rods 184 is shown in FIG. 10, due to the perspective of the drawing. The tension rods 184 each have a tool attachment end 186 which is pivotally attached to the tensile force application end 180 of a respective one of the levers 174, and an opposite clavicle attachment arm end 188 which temporarily secures into a respective tension rod attachment hole or passage 190 formed in the ends of each of the clavicle attachment arms 34 and 36; the tension rod attachment holes 190 are specifically indicated in FIGS. 1, 2, 6, and 10 and are visible in other drawings.

The clavicle attachment tool 172 and tension rods 184 are used generally as shown in FIG. 10. The clavicle attachment portion 104 of the prosthesis 100 (or other embodiment) is initially placed reasonably securely against the previously reshaped end of the clavicle C. The clavicle attachment arm ends 188 of the tension rods 184 are then temporarily and removably secured to their respective passages 190 in the ends of the two clavicle attachment arms 34 and 36. This defines the location along the clavicle C for the temporary placement of the clavicle attachment tool 172, which is then clamped removably to the clavicle C, generally as shown in FIG. 10. The two levers 176 (which may have only a single hand grip 176, if so desired) are then manipulated by squeezing toward the hand grip 178 of the clamping tool 172, which results in the tension rods 184 pulling the clavicle attachment component 104 tightly against the end of the clavicle C and locking the locking band 44 securely therein.

Once the clavicle attachment portion 104 of the prosthesis 100 has been pulled tightly against the end of the clavicle C, it may be permanently secured in place. Careful measurement has previously permitted the lateral screw passage L (shown in FIG. 9 of the drawings) to be drilled or otherwise formed at the proper location through the clavicle C, as described further above. The clavicle attachment screw 42 may then be installed through its countersunk hole 38 in the first clavicle attachment arm 34, and threaded into the opposite threaded hole or passage 40 (indicated in FIG. 1, and shown in other FIGS.) in the opposite second arm 36. The screw 42 includes a locking head, e.g. conventional teeth or the like formed in the underside of the head to engage the mating face of the countersunk hole 38, or other locking means as desired.

Once the screw 42 has been tightened, the clamping tool 172 may be released from the clavicle C and the clavicle arm attachment ends 188 of the two tension rods 184 removed from the clavicle attachment component arms 36 and 38 to complete the installation. The completed installation of the acromioclavicular joint prosthesis 100 of the present invention is illustrated in FIG. 10 of the drawings. Other embodiments, e.g. the embodiment 10 of FIG. 1, will be seen to install in a similar manner as that described for the prosthesis 100. The result is a durable and reliable prosthetic joint serving to secure the distal or outboard end of the clavicle to the acromion process of the scapula, to repair or replace that joint which has been previously damaged due to injury or disease.

It is to be understood that the present invention is not limited to the embodiments described above, but encompasses any and all embodiments within the scope of the following claims.

I claim:

1. An acromioclavicular joint prosthesis, comprising:
an acromion attachment component;
a clavicle attachment component; and
an articulated linkage connecting said acromion attachment component and said clavicle attachment component to one another;
a pair of mutually opposed, parallel clavicle attachment arms extending from said clavicle attachment component; and
a screw disposed through said clavicle attachment arms.

2. An acromioclavicular joint prosthesis, comprising:
an acromion attachment component;
a clavicle attachment component; and
an articulated linkage connecting said acromion attachment component and said clavicle attachment component to one another;
at least one acromion attachment and locking band extending from said acromion attachment component opposite said articulated linkage; and
an axially disposed clavicle insertion and locking band extending from said clavicle attachment component opposite said articulated linkage.

3. The acromioclavicular joint prosthesis according to claim 2, wherein said at least one acromion attachment and locking band comprises a single, axially disposed band having a free distal end.

4. The acromioclavicular joint prosthesis according to claim 2, wherein said at least one acromion attachment and locking band comprises an acromion-surrounding closed loop.

5. The acromioclavicular joint prosthesis according to claim 1, wherein said articulated linkage further includes a hinged joint.

6. The acromioclavicular joint prosthesis according to claim 1, wherein said articulated linkage further includes a spherical joint.

7. The acromioclavicular joint prosthesis according to claim 1, wherein said articulated linkage further includes an angularly displaceable locking joint.

8. The acromioclavicular joint prosthesis according to claim 1, wherein said articulated linkage further includes a linearly displaceable spring-loaded fitting.

9. The acromioclavicular joint prosthesis according to claim 1, further including an acromion installation tool.

10. The acromioclavicular joint prosthesis according to claim 1, further including a clavicle installation tool.

11. A method of reattaching the acromion to the clavicle of a patient using the apparatus of claim 1, comprising the steps of:
(a) reshaping the acromion to accommodate the acromion attachment component;
(b) reshaping the clavicle to accommodate the clavicle attachment component;
(c) permanently securing the acromion attachment component to the acromion; and
(d) permanently securing the clavicle attachment component to the clavicle.

12. A method of reattaching an acromion to a clavicle in a patient, comprising the steps of:
(a) providing a prosthesis having an acromion attachment component, a clavicle attachment component, and an articulated linkage connecting the acromion and clavicle attachment components to one another;
(b) reshaping the acromion to accommodate the acromion attachment component;
(c) reshaping the clavicle to accommodate the clavicle attachment component;
(d) permanently securing the acromion attachment component to the acromion; and
(e) permanently securing the clavicle attachment component to the clavicle.

13. The method of claim 12, further including the steps of:
(a) providing an acromion attachment and locking band extending from the acromion attachment component, opposite the articulated linkage;

(b) further providing a clavicle insertion and locking band extending from the clavicle attachment component, opposite the articulated linkage;
(c) locking the acromion attachment and locking band to the acromion;
(d) forming a generally axial clavicle insertion and locking band passage in the clavicle;
(e) inserting the clavicle insertion and locking band in the axial passage formed in the clavicle; and
(f) locking the clavicle insertion and locking band of the clavicle attachment component, within the clavicle.

14. The method of claim 13, further including the steps of:
(a) forming the acromion attachment and locking band as a single, axially disposed band;
(b) forming an acromion attachment and locking band slot through the acromion; and
(c) securing the acromion attachment and locking band within the acromion attachment band slot.

15. The method of reattaching the acromion to the clavicle of a patient according to the method of claim 14, further including the steps of:
(a) forming a clip installation passage through the acromion, generally normal to the acromion attachment and locking band slot; and
(b) installing a clip in the clip installation passage of the acromion and through the acromion attachment and locking band.

16. The method of claim 13, further including the steps of:
(a) forming the acromion attachment and locking band as a closed loop;
(b) passing the closed loop band around the acromion; and
(c) tightening and securing the closed loop band about the acromion.

17. The method of claim 13, further including the steps of:
(a) providing an acromion installation tool; and
(b) tightening and securing the acromion attachment and locking band to the acromion using the acromion installation tool.

18. The method of reattaching the acromion to the clavicle of a patient according to the method of claim 12, further including the steps of:
(a) providing a pair of mutually opposed, parallel clavicle attachment arms extending from the clavicle attachment component; and
(b) installing a locking screw through the clavicle attachment arms and the clavicle.

19. The method of reattaching the acromion to the clavicle of a patient according to the method of claim 18, further including the steps of:
(a) providing a clavicle installation tool;
(b) removably attaching the clavicle installation tool securely to the clavicle and to the clavicle attachment arms of the clavicle attachment component; and
(c) pulling the clavicle attachment component tightly against the end of the clavicle by means of the clavicle installation tool.

* * * * *